US00PP23583P2

(12) United States Plant Patent
Beckman et al.

(10) Patent No.: US PP23,583 P2
(45) Date of Patent: May 7, 2013

(54) PEACH ROOTSTOCK NAMED MP-29

(50) Latin Name: ***Prunus* species hybrid×*Prunus persica***
Varietal Denomination: MP-29

(75) Inventors: Thomas G. Beckman, Warner Robins, GA (US); Jose X. Chaparro, Gainesville, FL (US); Wayne B. Sherman, Gainesville, FL (US)

(73) Assignees: The United States of America, as represented by the Secretary of Agriculture, Washington, DC (US); Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/930,354

(22) Filed: Jan. 4, 2011

(51) Int. Cl.
*A01H 5/00* (2006.01)

(52) U.S. Cl. ..... Plt./180

(58) Field of Classification Search ..... Plt./180, Plt./194, 187, 181, 184, 186
See application file for complete search history.

*Primary Examiner* — Howard Locker
(74) *Attorney, Agent, or Firm* — Gail E. Poulos; John D. Fado; Lesley Shaw

(57) ABSTRACT

A new and distinct peach rootstock 'MP-29', which is an interspecific hybrid rootstock *Prunus* species hybrid×*Prunus persica*, which was developed for use as a clonal commercial rootstock under peach cultivars. It is distinguished by its resistance to peach tree short life/bacterial canker complex, Armillaria root rot, and to several species of root-knot nematodes.

5 Drawing Sheets

Latin name of the genus and species: The peach rootstock of this invention is botanically identified as an inter-specific hybrid, 'Edible Sloe' plum (*Prunus* species hybrid)× 'SL0014' (*Prunus persica*).

Variety denomination: The variety denomination is 'MP-29'.

BACKGROUND OF THE INVENTION

The present invention is to a new and distinct peach rootstock which is named 'MP-29'. 'MP-29' is an interspecific hybrid developed by the United States Department of Agriculture, Agricultural Research Service (USDA-ARS) at Byron, Ga. from a cross (R94542) made in 1994 between a *Prunus* plum species hybrid ('Edible Sloe' plum) and *Prunus persica* ('SL0014' peach) both unpatented.

The seed was stratified and germinated in the greenhouse and the seedling (initially designated R94542.09) planted in a nursery in the spring of 1995 at the USDA-ARS in Byron, Ga. The nursery grown tree was then moved to a field plot in the spring of 1996 at the same location. This tree was subsequently propagated by budding onto a peach seedling rootstock and both the original seedling tree and its budded counterparts were used as a source of hardwood and softwood cuttings. Asexual propagation of the new cultivar by budding at Bryon, Ga. has shown that all characteristics of the new cultivar are reproduced true to type and in firmly fixed form. Clonal propagation success varies but typically results in approximately 70-80% usable rooted cuttings.

BRIEF SUMMARY OF THE INVENTION

All major color code designations are made with reference to the "PANTONE Book of Color", published by H. N. Abrams, Inc., N.Y., 1990.

The present invention provides a novel peach rootstock having the characteristics illustrated herein. The rootstock 'MP-29' is an interspecific hybrid developed at the USDA in Byron, Ga. from an interspecific cross between a *Prunus* species hybrid ('Edible Sloe' plum) and *Prunus persica* ('SL0014' peach). 'MP-29' is graft compatible with peach (*P. persica*) scion cultivars and confers moderate vigor control of approximately 30-40% to the scion cultivar. It provides resistance to several soil borne diseases including Armillaria root rot (*A. tabescens*), peach tree short life/bacterial canker complex and several species of root-knot nematodes (*Meloidogyne incognita* and *M. floridensis*). Peach trees grown on this rootstock are productive but lower vigor than those on a standard rootstock such as 'Guardian'. 'MP-29' displays intermediate characteristics between typical plum and peach cultivars. It does not produce any fruit and is useful only as a rootstock.

DETAILED DESCRIPTION OF THE INVENTION

Figure 1:
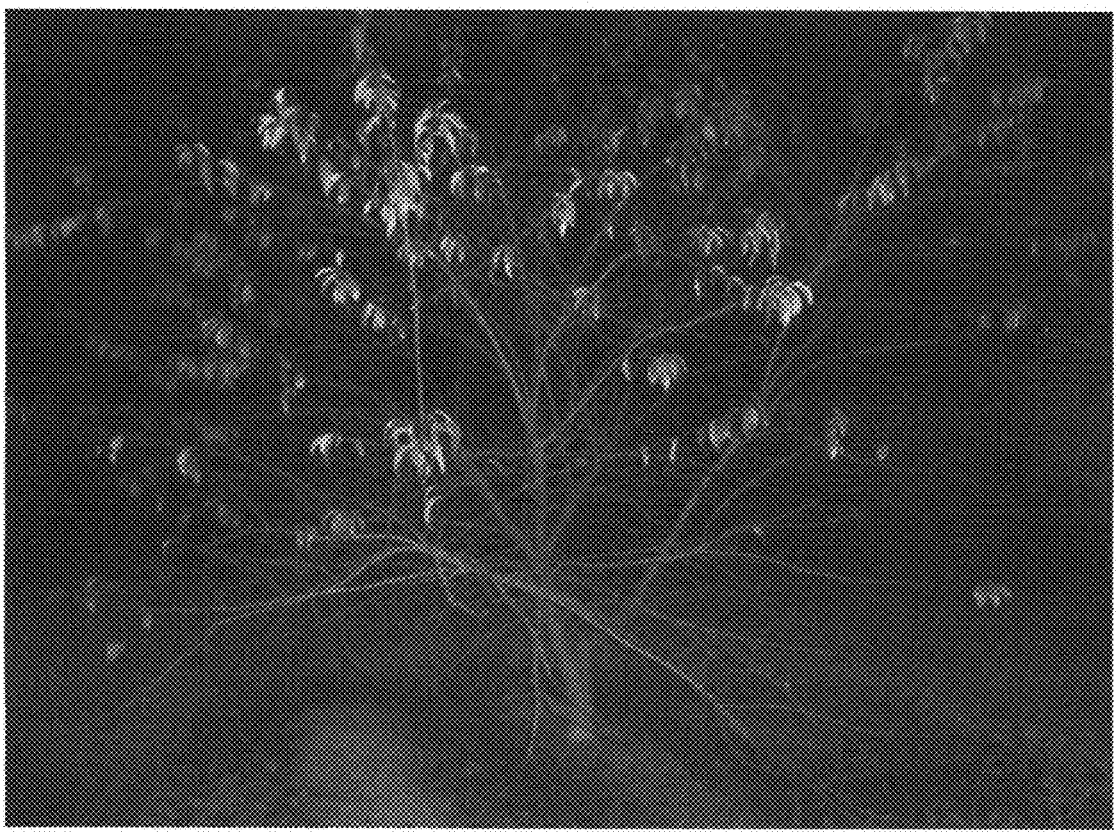
FIG. 1 illustrates the open, semi-spreading tree architecture of a 6-year-old tree of 'MP-29' budded onto Lovell peach seedling rootstock. Tree has been minimally 'pruned' during the collection of cuttings and the removal of low hanging limbs to facilitate equipment passage.
Figure 2:
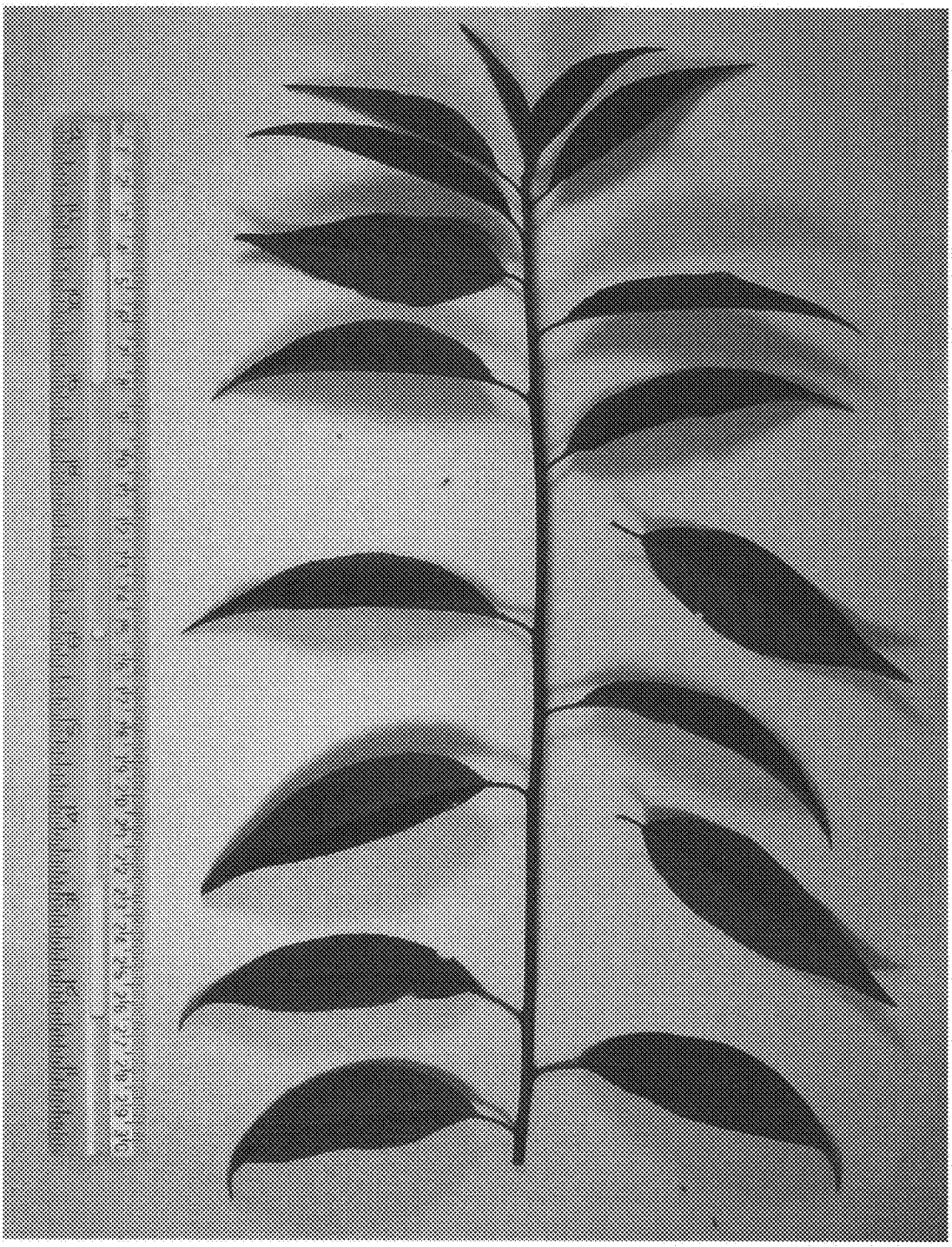
FIG. 2 illustrates an intact early season shoot of 'MP-29'. Two leaves have been detached and placed upper leaf surface side down to show the lower leaf surface.
Figure 3:
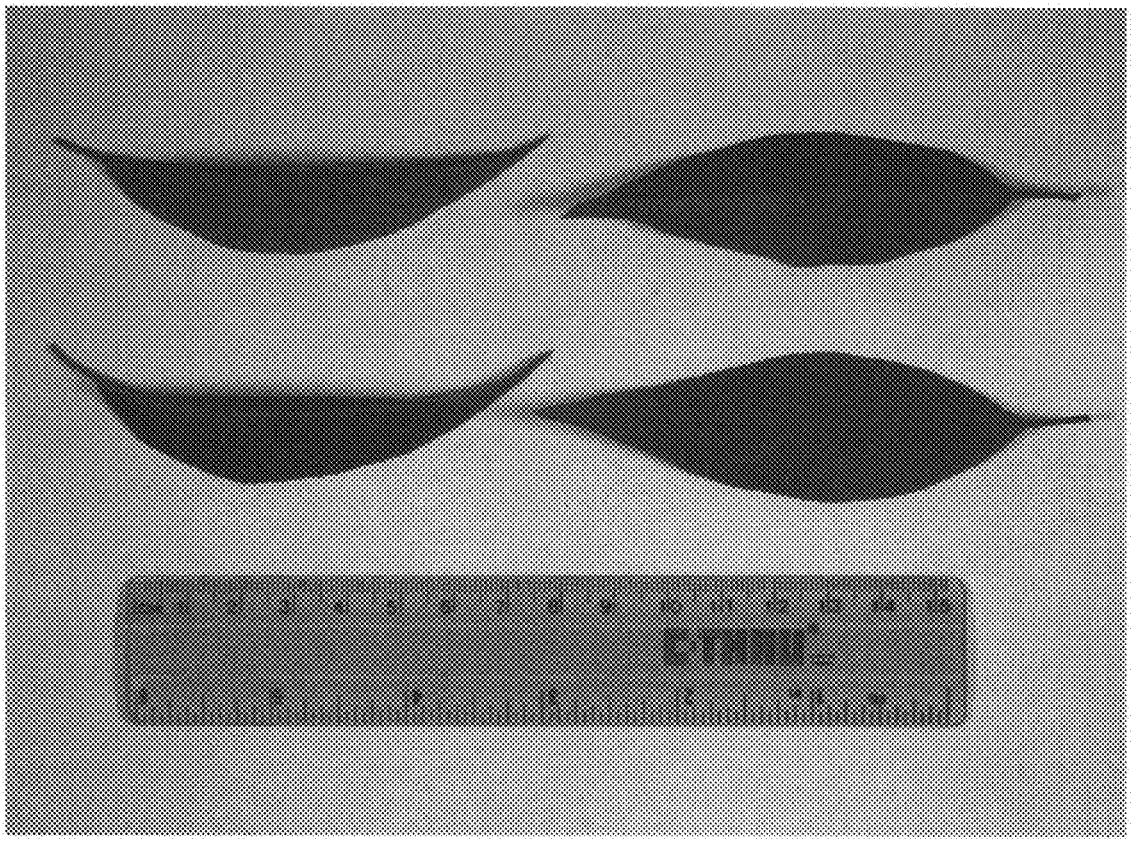
FIG. 3 illustrates a close up of the upper (L) and lower (R) leaf surface of leaves from a young early season shoot of 'MP-29'.
Figure 4:
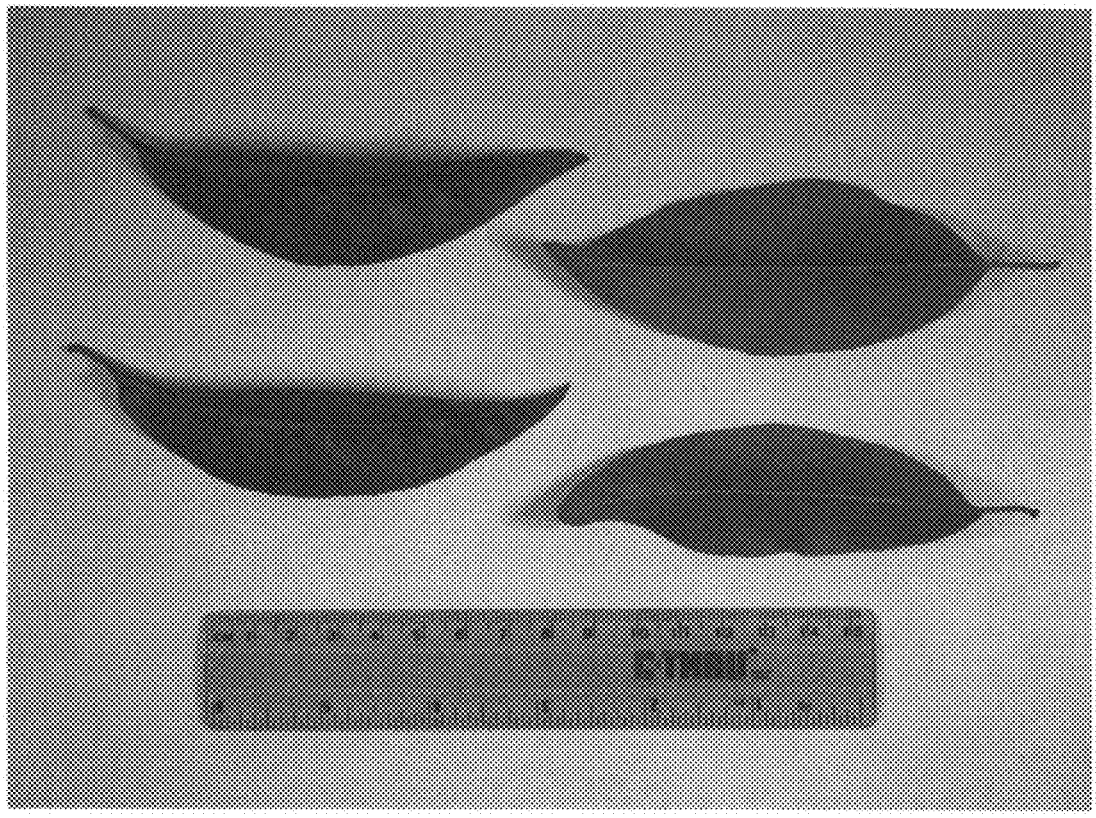
FIG. 4 illustrates a close up of the upper (L) and lower (r) leaf surface of leaves from a mature late season shoot of 'MP-29'.
Figure 5:
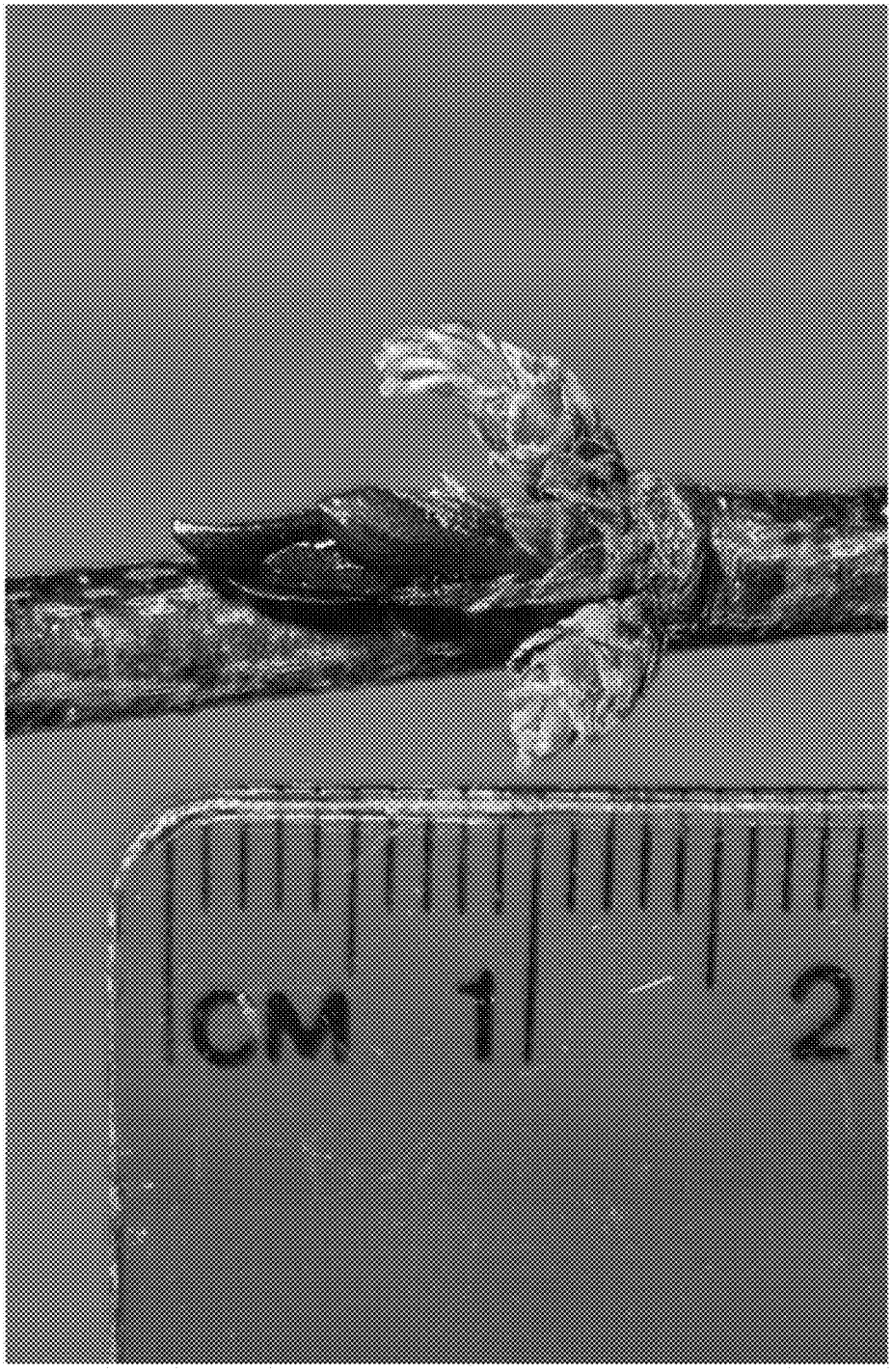
FIG. 5 illustrates a close up of MP-29 flowers.

In 1997 rooted cuttings of 'MP-29' were topworked with budwood of 'Flordaguard' peach rootstock and observed for signs of graft incompatibility. No signs of incompatibility were observed the following two seasons and 'MP-29' was advanced for further testing. In 1999, rooted cuttings of 'MP-29' were planted in a nursery and budded with virus indexed wood of 'Redhaven' peach. Finished trees were then planted in the spring of 2000 into two field sites at the Byron location.

The first was a site with a known history (as demonstrated by a previous peach planting) of both peach tree short life/bacterial canker complex and Armillaria root rot (*A. tabescens*). This planting was a well replicated trial with five tree plots of each rootstock treatment, i.e. 'MP-29', 'Sharpe', and 'Guardian' peach seedling rootstock. Trees in this planting were observed over subsequent years for the presence of dead and dying trees which were inspected to determine cause of death. Survival data from this trial is summarized below in Table 1. In this trial 'MP-29' has provided resistance to peach tree short life/bacterial canker complex (PTSL) numerically superior to but not statistically different from 'Guardian' peach rootstock or 'Sharpe' plum hybrid rootstock. However, 'MP-29' has provided significantly better resistance to Armillaria root rot (ARR) than has 'Guardian' peach rootstock. 'MP-29' provided resistance to Armillaria that was numerically better than that provided by 'Sharpe' rootstock but difference was not statistically significant.

The second site had no known history of either Armillaria root rot or peach short tree life/bacterial canker complex. This planting was a well replicated trial with single tree plots of the same rootstock treatments. Trees in this trial were trained to a 2-arm open center system and otherwise managed according to standard commercial practices. Supplemental drip irrigation was provided as needed in this trial only. This planting was thinned and harvested each year to determine the horticultural characteristics of each scion/rootstock combination. Horticultural data for this trial are summarized in Table 2 below. Rootstock suckers appearing around each tree were counted and removed each fall. After 7 growing seasons, trees on 'MP-29' have displayed a significant reduction in vigor, providing trees approximately 60% the size of those on 'Guardian' peach rootstock, similar to those on 'Sharpe' plum hybrid rootstock. Annual yield of trees on 'MP-29' rootstock has been similar to those of trees on 'Guardian' peach rootstock and statistically superior to those of trees on 'Sharpe' plum hybrid rootstock when expressed on a per tree basis. However, when productivity is expressed as cumulative yield efficiency (CYE), i.e. total cumulative yield divided by trunk cross-sectional area (TCSA), the productivity of trees on 'MP-29' rootstock is significantly greater than both those on 'Guardian' peach rootstock and those on 'Sharpe' plum hybrid rootstock. Average size of fruit from trees on 'MP-29' rootstock has not been significantly different from that of trees on 'Guardian' peach rootstock and has been significantly larger than that of trees on 'Sharpe' plum hybrid rootstock. Cumulative rootstock sucker counts have been numerically lower for trees on 'MP-29' than those on 'Guardian' peach rootstock or 'Sharpe' plum hybrid rootstock but differences have not been statistically significant.

Since these initial field trials utilizing the scion cultivar 'Redhaven' (now in their 11$^{th}$ year), rooted cuttings of 'MP-29' have been budded with several commercial peach cultivars, including 'Cresthaven', 'Delta', 'Faye Elberta', 'Fireprince'. 'Harvester', 'Majestic', and 'Redglobe' which were then observed for signs of graft incompatibility. Observation periods of each of these scion/rootstock combinations has ranged from 2-4 years and are continuing. To date no signs of incompatibility have been observed between 'MP-29' and any of the peach scion cultivars tested.

TABLE 1

Survival of advanced *Prunus* rootstock selections on an Armillaria (ARR) and Peach Tree Sort Life (PTSL) infested field site in Georgia[z] (2000-2008, Byron, GA).

| | | | Cause of Death | | |
|---|---|---|---|---|---|
| Rootstock | n | Alive (%) | ARR (%) | PTSL (%) | Other (%) |
| MP-29 | 50 | 64 | 10 | 2 | 24 |
| Sharpe | 50 | 50 | 24 | 14 | 12 |
| Guardian[y] | 50 | 26 | 58 | 6 | 10 |
| MSD[x] | | 28 | 23 | ns | ns |

[z]Est. Spring 2000 with 5 tree plots in a RCB design, budded with 'Redhaven'.
[y]Guardian selection SL2891, a component of the bulk commercial seedlot.
[x]Minimum significant difference (Waller-Duncan, k-ratio = 100).
ns = not significant

TABLE 2

Horticultural performance of 'Redhaven' peach propagated on advanced *Prunus* rootstock selections in central Georgia[z] (2000-2006, Byron, GA).

| Rootstock | TCSA[y] ($cm^2$) | Size (% of Std.) | Yield[x] (kg/tree) | CYE[w] ($Kg/cm^2$) | Fruit Size (gm) | Suckers[v] (#/tree) |
|---|---|---|---|---|---|---|
| Guardian | 159 | 100 | 69 | 0.46 | 150 | 9 |
| MP-29 | 100 | 63 | 63 | 0.63 | 146 | 2 |
| Sharpe | 99 | 62 | 29 | 0.30 | 131 | 7 |
| MSD[u] | 31 | — | 9 | 0.10 | 16 | ns |

[z]Est. Spring, 2000 with 8 single tree plots in a RCB design.
[y]Trunk cross-sectional area (Fall, 2006).
[x]Cumulative yield from 2002 through 2006 season (no crop in 2007 due to late freeze).
[w]Cumulative yield efficiency through 2006 season.
[v]Cumulative number through Fall, 2006.
[u]Minimum significant difference (Waller-Duncan, k-ratio = 100)
ns = not significant

BOTANICAL DESCRIPTION OF THE PLANT

The following horticultural description was developed from plant material of the new cultivar growing in Byron, Ga. Trees of 'MP-29' were observed during the 2010 growing season. At that time the trees were approximately six years old. Color definitions used throughout the following description are from "The PANTONE Book of Color", published H. N. Abrams, Inc., N.Y. 1990.

Trees: The trees from which this description has been made were planted at the SEFTNRL as a source of cutting material from which to propagate the new rootstock for experimental test plantings. Seedlings of 'Lovell' peach rootstock were planted in a fumigated nursery at the Byron location in the spring of 2004 and budded in early summer with wood of 'MP-29'. The propagated trees were transplanted to their present location in the spring of 2005 and grown with conventional fertilizer, weed and insect management practices with only light pruning applied to eliminate low limbs that might interfere with the passage of equipment. No supplemental irrigation has been applied. Since planting the individual trees have received varying levels of annual pruning during the collection of cuttings but overall pruning has been light, substantially less than that a normal commercial peach cultivar would routinely receive.

*Ploidy*.—Diploid.

*Size*.—Trees are medium stature after six growing seasons on 'Lovell' rootstock when minimally pruned. Average trunk caliper at the end of six growing seasons is approximately 18.3 cm. Average height is approximately 5.0 m. Average tree spread across rows is approximately 5.1 m and down the tree row is approximately 5.4 m.

*Vigor*.—Trees are moderately vigorous when budded to 'Lovell' rootstock. Trees readily produce long shoots suitable for cuttage.

*Density*.—Trees have a light branching habit which promotes the growth of long whips suitable for cuttage.

*Form*.—Tree form is open and semi-spreading.

*Hardiness*.—Hardy with respect to middle Georgia winters where the historical average minimum temperature of the coldest month (January) is approximately 2.1 C.

*Chilling requirement*.—Estimated endodormancy chilling requirement is about 750 chill hours (below approximately 7 C) based on time of vegetative bud break relative to standard peach varieties.

Trunk: At six years of age the trunk surface is somewhat rough and shaggy in spots with a netting pattern of cracks in the older bark which exposes a lighter bark beneath.

*Size*.—After six growing seasons the average trunk caliper is approximately 18.3 cm at a height of approximately 30 cm.

*Texture*.—Medium rough and occasionally shaggy in spots.

*Bark*.—Older bark is grayish brown (Pantone 17-1312, Silver Mink). Exposed bark in cracks is medium brown (Pantone 18-1154, Glazed Ginger).

*Lenticels*.—Moderately high in number, averaging approximately 2.9/cm$^2$ of trunk surface. Shape is roughly elliptical. Average length is approximately 5.62 mm×1.61 mm thick, with the long axis oriented perpendicular to the long axis of the shoot. Color is light brown (Pantone 16-1150, Topaz).

Scaffold branches:

*Size*.—Strong growth of scaffold branches.

*Texture*.—Similar to trunk but generally smoother. Similar netting pattern and bark color.

1-year old shoots:

*Size*.—Tree readily produces long shoots suitable for use in cuttage. Average length of shoots in well exposed portions of the canopy is approximately 1.08 m with an average basal caliper of approximately 8.5 mm.

*Texture*.—Shoots are initially smooth but a fine cracking in cuticle gradually develops as shoot matures developing by season's end into a net-like pattern particularly in the basal portion of each shoot resulting in a rougher appearance.

*Color*.—Initial color of extending shoot is a dark purplish red (Pantone 19-1606, Raisin) but by the end of the growing season the apical portion of the current season's shoot fades to a dark reddish brown (Pantone19-1518, Puce) on the sun exposed surfaces and a medium green on the shaded side (Pantone 15-0332, Leaf Green). Late season the basal portion of the current season's shoot is more mottled in appearance with a lighter reddish brown color (Pantone 18-1137, Rawhide) and the silvery-grey, semi-transparent cuticle now being shed in places.

*Lenticels*.—Initially not observable but by the end of the season very small, roughly elliptical lenticels can be seen on the basal portions of current season's growth. Average length is approximately 0.89 mm×0.42 mm thick with the long axis oriented perpendicular to the long axis of the shoot. Color is a light tan (Pantone 13-1010, Gray Sand).

Leaves:

*Size*.—0.14 mm thick blade. Measurements were made on leaves collected from the mid-shot position of well exposed vigorous shoots.

*Form*.—Lanceolate.

*Apex*.—Acuminate.

*Base*.—Cuneate.

*Margin*.—Serrulate.

*Surface*.—Upper, glabrous, lower, medium large veins that are pinnately netted with light pubescence along midrib at junction with leaf blade. Initially midrib is a dark purplish red (Pantone 19-1606, Raisin), fading later in season to a more pinkish red (Pantone 17-1641, Chrysanthemum) and finally a pale yellow (Pantone 12-0714, Cornhusk) in late summer.

*Color*.—Upper leaf surface initially dark purplish red (Pantone 19-1606, Raisin) , fading later in season to dark green (Pantone 18-0430, Avocado) near apex or somewhat lighter green (Pantone 17-0336, Peridot) on basal leaves. Lower leaf surface initially a medium purplish red (Pantone 18-1426, Pompeii), fading later in season to a medium green (Pantone 18-0332, Grasshopper) near apex or somewhat lighter green (Pantone 17-0336, Peridot) on basal leaves.

*Glands*.—Typically 1 or 2 very small (<approximately 1 mm tall) reniform glands on petiole near leaf blade.

*Petiole*.—Average approximately 12.6 mm in length and approximately 1.3 mm thick. Grooved longitudinally on upper surface with a light pubescence on the edges of the groove. Initially dark purplish in color (Pantone 19-1606, Raisin), later fading to a pinkish red (Pantone 17-1641, Chrysanthemum) and finally a pale yellow (Pantone 12-0714, Cornhusk) by late summer.

*Stipules*.—Initially present, dark purplish red (Pantone 19-1606, Raisin), approximately 5-7 mm in length. Typically shed by the time the leaf is fully expanded.

*Arrangement*.—Alternate.

Buds:

*Abundance*.—Typically 1-3 per node, occasionally more.

*Size*.—Average approximately 4.1 mm in length and approximately 1.9 mm thick.

*Form*.—Plump, conical.

*Surface*.—Pubescent scales.

*Color*.—Reddish Brown (Pantone 18-1137, Rawhide)

Flowers and fruit: Flowers are rarely observed on 'MP-29' and, fruit have never been produced. 'MP-29' is evidently sterile, most likely the result of the wide interspecific parentage of the new cultivar. Flowers when present, typically appear singly or in pairs of discrete buds flanking a vegetative bud much like the typical arrangement in peaches rather than the compound buds (vegetative and multiple flowers combined) typical of plums. Most years flower buds abscise just as vegetative buds break. Flowers: No sepals, petals or anthers present, only pistils (usually multiple). Pistils have a yellow-greenish (Pantone 16-742, Green Sulphur). Under prolonged exposure to sun the stigma develops a reddish-brown color (Pantone 19-1334, Henna). Number of pistils per flower bud ranges from about 7 to about 15, averaging about 13. Length ranges from about 3 to about 10 mm, averaging about 6 mm.

Resistance to disease: 'MP-29' has significant resistance to both peach tree short life/bacterial canker complex, comparable, if not superior to 'Guardian' peach rootstock, the current standard for comparison in this regard. 'MP-29' has significantly better resistance to Armillaria root rot (*A. tabescens*) than typical commercial peach seedling rootstock type such as 'Guardian'. Additionally, in field trials at the Byron location and in northern Florida infested with root-knot nematodes (*Meloidogyne incognita* and *M. floridensis*, respectively) 'MP-29' displayed no visible galling while known susceptible rootstocks in the same trials were severely galled.

We claim:

1. A new and distinct interspecific peach rootstock plant 'MP-29' as illustrated and described herein.

* * * * *